US010272181B2

(12) United States Patent
Gavard Molliard

(10) Patent No.: US 10,272,181 B2
(45) Date of Patent: Apr. 30, 2019

(54) METHOD FOR OBTAINING AN INJECTABLE HYDROGEL BASED ON HYALURONIC ACID CONTAINING LIDOCAINE AND AN ALKALINE AGENT, STERILIZED WITH HEAT

(71) Applicant: ANTEIS S.A., Plan-les-Ouates (CH)

(72) Inventor: Samuel Gavard Molliard, Bogève (FR)

(73) Assignee: ANTEIS S.A., Plan-les-Ouates (CH)

(*) Notice: Subject to any disclaimer, the term of this patent is extended or adjusted under 35 U.S.C. 154(b) by 0 days.

(21) Appl. No.: 15/024,433

(22) PCT Filed: Sep. 26, 2014

(86) PCT No.: PCT/EP2014/002628
§ 371 (c)(1),
(2) Date: Mar. 24, 2016

(87) PCT Pub. No.: WO2015/043757
PCT Pub. Date: Apr. 2, 2015

(65) Prior Publication Data
US 2016/0228613 A1  Aug. 11, 2016

(30) Foreign Application Priority Data
Sep. 27, 2013  (FR) .................................... 13 59338

(51) Int. Cl.
A61L 27/52 (2006.01)
A61K 8/04 (2006.01)
A61K 8/42 (2006.01)
A61K 9/00 (2006.01)
A61Q 19/08 (2006.01)
A61L 27/54 (2006.01)
A61L 27/20 (2006.01)
A61K 9/06 (2006.01)
A61K 31/167 (2006.01)
A61K 8/73 (2006.01)
A61K 47/36 (2006.01)
A61L 27/50 (2006.01)

(52) U.S. Cl.
CPC .............. A61L 27/54 (2013.01); A61K 8/042 (2013.01); A61K 8/42 (2013.01); A61K 8/735 (2013.01); A61K 9/0019 (2013.01); A61K 9/0024 (2013.01); A61K 9/0048 (2013.01); A61K 9/06 (2013.01); A61K 31/167 (2013.01); A61K 47/36 (2013.01); A61L 27/20 (2013.01); A61L 27/50 (2013.01); A61L 27/52 (2013.01); A61Q 19/08 (2013.01); A61K 2800/91 (2013.01); A61L 2300/402 (2013.01); A61L 2400/06 (2013.01); A61L 2430/02 (2013.01); A61L 2430/22 (2013.01); A61L 2430/34 (2013.01)

(58) Field of Classification Search
None
See application file for complete search history.

(56) References Cited

U.S. PATENT DOCUMENTS

| 5,916,583 | A | * | 6/1999 | Broberg | A61K 9/0014 424/422 |
| 8,357,795 | B2 | * | 1/2013 | Lebreton | A61K 8/42 424/488 |
| 8,450,475 | B2 | * | 5/2013 | Lebreton | A61K 8/42 424/484 |
| 2009/0155362 | A1 | * | 6/2009 | Longin | C08B 37/0072 424/484 |
| 2011/0118206 | A1 | * | 5/2011 | Lebreton | A61K 8/42 514/54 |
| 2012/0071437 | A1 | | 3/2012 | Stroumpoulis | |

FOREIGN PATENT DOCUMENTS

WO  WO 2010/015901  2/2010
WO  WO 2010/052430  3/2010

OTHER PUBLICATIONS

Beer, "New fillers with anesthetic", The Dermatologist, 2010, pp. 1-7.*
Ballin, A.C., et al. Clinical, Cosmetic and Investigational Dermatology, vol. 6, p. 183-189, Aug. 2, 2013.
International Search Report for PCT/EP2014/002628 dated Oct. 22, 2014.

* cited by examiner

Primary Examiner — Ernst V Arnold
Assistant Examiner — Kyung S Chang
(74) Attorney, Agent, or Firm — Hueschen and Sage

(57) ABSTRACT

The object of the present invention is a method for obtaining an injectable hydrogel based on hyaluronic acid containing lidocaine hydrochloride and an alkaline agent, sterilized with heat, having hyaluronic acid concentration and flow properties, equivalent to those of the corresponding hydrogel based on hyaluronic acid not containing any lidocaine hydrochloride. The present invention also relates to various uses of the aforementioned hydrogel.

21 Claims, No Drawings

METHOD FOR OBTAINING AN INJECTABLE HYDROGEL BASED ON HYALURONIC ACID CONTAINING LIDOCAINE AND AN ALKALINE AGENT, STERILIZED WITH HEAT

The present invention relates to a method for making an injectable hydrogel based on hyaluronic acid containing lidocaine and an alkaline agent, sterilized with heat, to the gel thereby obtained, as well as to its use in the therapeutic and esthetic fields.

The use of injectable hydrogels based on hyaluronic acid is common for separating, replacing or filling a biological tissue or increasing the volume of said tissue, and also for supplementing or replacing a biological fluid.

Thus, the viscoelastic products based on hyaluronic acid are used in many therapeutic applications and in the dermato-cosmetic field.

For example, these products based on crosslinked or non-crosslinked hyaluronic acid are used:
  in rheumatology, as a replacement agent, a temporary supplement for synovial liquid,
  in urology/gynecology, as an agent allowing an increase in the volume of the sphincter or of the urethra,
  in ophthalmology, as an adjuvant for cataract surgery or for treating glaucomas,
  in pharmaceutics, as a gel for releasing active substances,
  in surgery, for bone reconstruction, increase in the volume of vocal chords or for the making of surgical tissues,
  in dermato-cosmetics, for filling wrinkles, hiding scars or increasing the volume of lips.

The hyaluronic acid concentration and the flow properties of a hydrogel are essential properties for an injectable product based on hyaluronic acid. These properties for the major part condition the structure of this product and therefore its application and its performance. Thus, the elastic modulus (G') and viscous modulus (G") are important characteristics for an injectable hydrogel based on hyaluronic acid as indicated in the following publication:

Sundaram H. et al., *Comparison of the rheological properties of viscosity and elasticity in two categories of soft tissue fillers: calcium hydroxyapatite and hyaluronic acid*, Dermatologic surgery, 2010, 36 (S3), 1859-1865.

Lidocaine is a local anesthetic currently used in the aesthetic and medical field. This molecule has notably been used for many years in products with an aesthetical purpose such as products for filling wrinkles, in order to limit pain during or after injection. For example, the products Zyderm®/Zyplast® based on collagen and on 0.3% of lidocaine have been marketed for more than 20 years.

Recently, lidocaine was introduced into novel formulations based on hyaluronic acid used in dermato-cosmetics for filling wrinkles and restoring volumes (cases of the products Juvéderm® Utra 2/3/4, Prevelle® Silk/15 Shape, Elevess®, . . . ). In all of these products, the presence of lidocaine does not challenge the known functions of these medical devices, which is to fill skin depressions. Lidocaine, by its anesthetic activity, allows improvement in the patient's comfort by limiting the pain during and after injection of the product.

It is interesting to specify that many practitioners either do not use gels based on hyaluronic acid containing lidocaine (for example when the presence of lidocaine is a counter-indication in patients having known sensitivity to this compound), or consider that they do not need this anesthetic action, since they use other means for managing pain like truncular nerve anesthesia, the use of a less traumatic injection technique or device, or indeed the use of an anesthetic product for topical application.

Nevertheless, at the present time, the products for filling wrinkles and restoring volumes based on hyaluronic acid made available to practitioners do not provide the possibility of considering lidocaine as an option since they do not provide the possibility to practitioners of selecting a given product with or without lidocaine. By a given product reference is made to gels with or without lidocaine having substantially equal hyaluronic acid concentration and (equivalent) flow properties and therefore allowing practitioners to have the same clinical applications and performance during the injection and in post-injection for the version with and without lidocaine (except for the beneficial effects on pain induced by the presence of lidocaine). Indeed, on the market, a large number of these products only exist in a version with lidocaine (case of the products Juvéderme Ultra 2/3/4, Prevelle® and Elevess®).

This situation notably leads many practitioners to incorporate lidocaine themselves in commercial products not containing any, in order to be able to treat their patients with injectable products which they desire while having the beneficial effects of the anesthetic. For the practitioner this involves mixing the gel based on injectable hyaluronic acid with a lidocaine solution (for example injectable Xylocaine®) just before its injection into the patient, which notably induces dilution of the hydrogel (decrease in the hyaluronic acid concentration) and a substantial modification of the flow properties of the commercial product.

For commercial products based on hyaluronic acid containing lidocaine (an anesthetic incorporated during the manufacturing of the product), the prior art teaches methods allowing introduction of lidocaine in the form of an aqueous solution in a gel based on hyaluronic acid.

These methods are however are not totally satisfactory since they also actually lead to a dilution of the injectable hydrogel and to significantly modified flow properties. In particular an increase in elasticity (increase in the value of the elastic modulus G') and an increase in elastic nature (decrease of the G"/G' ratio) of the hydrogel are observed, which may be undesirable depending on the conditions being treated (for example, a too elastic injectable product i.e. having too high a G' modulus and/or too low a G"/G' ratio, may give rise to areas felt by the patient as hard and/or uncomfortable, or even painful.

The goal of the present invention is therefore to propose a method for preparing an injectable hydrogel based on hyaluronic acid, or one of its salts, and on lidocaine, by incorporating lidocaine and an alkaline agent in a gel of hyaluronic acid without significant modifications of the essential properties of the product which are the hyaluronic acid concentration and the flow properties of viscoelasticity, i.e. the values of the moduli G' and G" of the relevant hydrogel.

For this purpose, the method for preparing an injectable hydrogel (therefore sterile) based on crosslinked hyaluronic acid, or one of its salts, and on lidocaine, according to the present invention comprises the following successive steps:
i) making a gel based on crosslinked hyaluronic acid or one of its salts,
ii) adding lidocaine hydrochloride as a powder or as a solution in said gel and then mixing,
iii) adjusting the pH to a value of between 6.5 and 7.6 by adding an alkaline agent in the gel+lidocaine hydrochloride mixture, and homogenizing the whole mixture, providing the possibility of obtaining a hydrogel not containing any suspended solid lidocaine particles, iv) sterilizing the hydrogel with heat.

This method according to the invention differs, in particular, in the time and form (solid/liquid) of lidocaine addition.

Such a method for adding lidocaine hydrochloride, particularly in solid form (powder), associated with the addition of an alkaline agent, quite surprisingly gives the possibility, starting from a given gel of crosslinked hyaluronic acid, of obtaining a hyaluronic acid concentration and flow properties G' and G" of this gel including the lidocaine hydrochloride, equivalent to those of the same gel without lidocaine hydrochloride. With this method it is therefore possible not to modify the fundamental properties conditioning the performance of said gel.

The method of manufacture according to the invention involves a gel based on hyaluronic acid or on a salt of hyaluronic acid preferably prepared and crosslinked according to the techniques described in the prior art. Mention may for example be made of the crosslinked gels according to WO 2005/085329 and the crosslinked and grafted gels according to WO 2005/012364.

According to a particular embodiment of the invention, the crosslinking is accomplished by bi- or poly-functional molecules for example selected from epoxides, epihalohydrins and divinylsulfone, acting on hyaluronic acid or one of its salts, not crosslinked or already crosslinked, with or without one or several other polysaccharides of natural origin. Advantageously, crosslinking is accomplished with butanediol diglycidyl ether.

The crosslinking degree of a hydrogel based on hyaluronic acid or on one of its salts is defined as being the mass ratio, expressed as a percentage, of the mass of the crosslinking agent to the mass of hyaluronic acid or one of its salts, introduced into the reaction mixture during the preparation of the product.

According to a particular embodiment of the invention, the crosslinking degree of the hydrogel according to the invention is between 0.1% and 25%, preferably between 0.5% and 15% and advantageously between 1.5% and 14%.

According to a particular embodiment of the invention, the gel may also contain other bio-compatible polymers (like polysaccharides of natural origin) and/or other active or non-active substances having a positive effect on the body or on the gel.

Among the preferred salts of hyaluronic acid according to the invention, mention will be made of the salts of hyaluronic acid, with a cation notably a mono- or di-valent cation selected from sodium, potassium, magnesium, calcium, manganese and/or zinc. Sodium salts are most particularly preferred.

In the method according to the invention, the hyaluronic acid concentration or of one of its salts obtained in step i) may be between 1 mg/ml and 50 mg/ml, preferably between 4 and 14 mg/ml, still more preferably between 14 and 35 mg/ml.

The molecular mass of the hyaluronic acid or of one of its salts used for making the hydrogel is between 1,000 Da and $10 \times 10^6$ Da, preferably between $2.10^5$ Da and $5.10^6$ Da, still more preferably between $5.10^5$ Da and $4.10^6$ Da.

The order of addition of the constituents to the gel based on hyaluronic acid is important: it is necessary to introduce the lidocaine hydrochloride into the gel and to proceed with mixing before adding the alkaline agent in order to adjust the pH to the values mentioned above (step iii). If not, a portion of the added lidocaine hydrochloride (added as a powder or as a solution with some undissolved lidocaine hydrochloride particles) remains in the form of solid particles, which do not dissolve. It is then not possible to obtain a translucent gel, i.e. without any lidocaine particles visible to the naked eye (suspended particles in the gel), as generally required for a large number of applications such as for example applications in the dermato-cosmetic field.

The concentration of lidocaine hydrochloride in the gel is advantageously between 0.1 and 50 mg/ml, preferably between 1 and 30 mg/ml, still more preferably between 2 and 20 mg/ml.

The alkaline agent may be introduced into the gel in solid form or in the form of a pure or diluted liquid. In the case of a diluted liquid, the alkaline agent is advantageously added in the form of an aqueous solution, sufficiently concentrated so as not to induce a dilution of the hyaluronic acid gel.

The amount of alkaline agent introduced into the gel notably depends on the type of selected alkaline agent, on the lidocaine hydrochloride concentration in the gel, on the pH of the gel before adding the lidocaine hydrochloride, on characteristics of the gel such as the hyaluronic acid concentration, and on desired flow properties G' and G" for the final products sterilized with heat. One skilled in the art will be able to select a suitable amount of alkaline agent for meeting the needs of the formulation which is being developed.

The alkaline agent is preferentially selected from sodium hydroxide, potassium hydroxide or sodium bicarbonate; advantageously, the selected alkaline agent is sodium hydroxide.

The gel with lidocaine according to the invention has an equivalent concentration of hyaluronic acid or of one of its salts to that of the gel not containing any lidocaine. Thus, in order to be considered as an equivalent in terms of hyaluronic acid concentration, the gel according to the invention, which has potentially been slightly diluted because of the addition of the alkaline agent (if the latter was added as a solution) should not have a dilution percentage of more than 2.5%, in order to be able to be considered as equivalent to the corresponding gel not containing any lidocaine.

The dilution percentage of the gel is defined in the following way:

Let V1=Volume of the added alkaline solution,

Let V2=Volume of gel after adding lidocaine hydrochloride and before adding the alkaline solution.

$$\text{Dilution percent} = V1 * 100/(V1+V2).$$

This dilution percentage of the gel following the addition of the alkaline agent, is advantageously less than or equal to 2.5%, preferably less than or equal to 1.5%, still more preferably less than or equal to 1%.

Advantageously, the pH of the hydrogel, before and after sterilization, is between 6.5 and 7.6, preferably between 6.9 and 7.5, still more preferably between 7.0 and 7.4, still more preferably between 7.1 and 7.3.

The sterilization of the gel is carried out with heat, preferably with humid heat. One skilled in the art will know how to select a heat sterilization cycle (temperature and duration of the sterilization cycle) suitable for sterilizing his/her product. For example, sterilization with humid heat may be carried out at 131° C. for 1 to 2 mins, at 130° C. for 3 mins, at 125° C. for 7 mins, at 121° C. for 20 mins, at 121° C. for 10 mins or at 100° C. for 2 hours.

The present invention also relates to a sterile injectable hydrogel based on hyaluronic acid or on one of its salts, on lidocaine hydrochloride and on an alkaline agent, prepared by the method described above, having flow properties (notably moduli G' and G") which substantially correspond to those of the same hydrogel not containing any lidocaine hydrochloride. Indeed, surprisingly, a gel based on hyaluronic acid, on lidocaine hydrochloride and on an alkaline agent obtained according to the invention has a hyaluronic acid concentration and a rheology (and therefore, a gel structure) equivalent to the gel without lidocaine hydrochloride. More practically, the hydrogel according to the present invention prepared according to the method described above, has a dilution percentage not exceeding 2.5%, preferably less than or equal to 1.5%, still preferably less than or equal to 1%, relatively to the same hydrogel without lidocaine hydrochloride.

The injectable hydrogel according to the invention may be used in the aesthetic (dermato-cosmetic) field or therapeutic field, more particularly for filling or replacing biological tissues or further for separating, replacing or filling a biological tissue or separating the volume of said tissue or further for supplementing or replacing a biological fluid. It may thus be used for example for filling wrinkles, remodeling the face or the body or increasing the volume of lips.

According to another alternative, the injectable hydrogel according to the invention may be used in the treatment for rehydrating skin by mesotherapy.

The hydrogel of the present invention may also be used in many therapeutic applications such as for example:
  in rheumatology, as a replacement agent, a temporary supplement for synovial liquid;
  in urology/gynecology, as an agent allowing an increase in the volume of the sphincter or of the urethra;
  in ophthalmology, as an adjuvant for cataract surgery or for treating glaucomas;
  in pharmaceutics, as a gel for releasing active substances;
  in surgery, for bone reconstruction, increase in the volume of vocal chords or for the making of surgical tissues;
  in dermato-cosmetics, for filling wrinkles, hiding scars or increasing the volume of lips.

For the whole of the indications mentioned above, the presence of lidocaine in the hydrogel allows an improvement to be achieved in the comfort of the patient during the injection and after the injection.

The invention is of major interest for injectable products based on hyaluronic acid, sterilized with heat, compliant with those already marketed and which require the incorporation of lidocaine in their compositions for reducing pain during and after injection. The method according to the invention thus provides the possibility of being able to propose commercially products with lidocaine, equivalent to those which do not contain any lidocaine, in terms of hyaluronic acid concentration and flow properties (notably the moduli G' and G") and thus without modifying the structure of the gels and therefore the performance of these products.

The method according to the invention with addition of the lidocaine, preferably as a powder, gives the possibility of varying the concentration of anesthetic without modifying the hyaluronic acid concentration, the alkaline agent being able to be introduced in a more concentrated form, without modifying the flow properties of said hydrogel.

The practitioner may thus have a palette of gels based on a same concentration of hyaluronic acid: without anesthetic on the one hand and with different concentrations of anesthetic such as lidocaine according to the desired use, on the other hand.

EXAMPLES

The invention is illustrated by the following, by no means limiting, examples.

The formulations prepared are gels based on crosslinked sodium hyaluronate (NaHA) in a buffered aqueous solution (composition: NaCl: 8.0 g/$Na_2HPO_4$, $12H_2O$: 2.4 g/$NaH_2PO_4$, $2H_2O$: 0.5 g/l liter of water for an injectable preparation), either containing lidocaine hydrochloride or not and an alkaline agent.

The sodium hyaluronate used for making these gels has a molecular mass equal to $2.5 \times 10^6$ Da or $3.1 \times 10^6$ Da. The crosslinking agent used is butanediol diglycidyl ether (BDDE) and the definition of the crosslinking degree used is: mass (BDDE)/mass (dry NaHA).

The incorporation into the gel of lidocaine hydrochloride as a powder is carried out by adding the required amount of compound (% expressed by mass) into the gel and by mixing with a spatula for 5 minutes (for 50 g of gel).

The incorporation of the alkaline agent into the gel is carried out by adding the required amount of the relative compound (% expressed by mass) in the form of alkaline aqueous solution in the gel and by mixing with a spatula for 5 minutes (for 50 g of gel).

The gels prepared are introduced into glass syringes and then sterilized in humid heat for 20 minutes at a temperature of 121° C. or for 2 minutes at a temperature of 131° C.

The rheometer used for carrying out the rheological characterizations (in a dynamic mode) is an AR2000 (TA Instruments) with a flat geometry of 40 mm, an air gap of 1,000 µm and an analysis temperature of 25° C.

Example 1

Demonstrating by Rheology the Structural Difference After Sterilization in Humid Heat Between Gels Based on Hyaluronic Acid with and without Lidocaine Hydrochloride and with Lidocaine Hydrochloride and Sodium Hydroxide Let A be a gel based on crosslinked NaHA.

This gel is obtained by hydrating sodium hyaluronate with a molecular mass of $2.5 \times 10^6$ Da in a 1% by mass soda aqueous solution of sodium hydroxide, by adding the crosslinking agent BDDE in order to obtain a crosslinking degree of 9%, by crosslinking for 2 h at 50° C. and by dialyzing the gel for 24 hours (regenerated cellulose, separation limit: Molar mass=60 kDa). The gel thereby obtained has a concentration of sodium hyaluronate of 22.5 mg/ml and a pH of 7.07.

After mixing for 10 minutes with a spatula, the gel A thereby obtained is divided into three fractions of equal mass (50 g).

Let B be fraction No.1. In this fraction, 0.3% of lidocaine hydrochloride as a powder is added. The gel is mixed with a spatula for 5 minutes. The pH is then 6.81.

Let C be fraction No.2. In this fraction, 0.3% of lidocaine hydrochloride is added as a powder and mixing is performed with a spatula for 5 minutes. Next 275 µl of a 1% by mass sodium hydroxide aqueous solution are added and mixing is performed with a spatula for 5 minutes. The pH is then equal to 7.27.

Let D be fraction No.3. The gel is mixed with the spatula for 10 minutes. A pH equal to 7.07 is measured.

The gels prepared are filled into a glass syringe and then sterilized with heat (121° C., 20 mins).

Let B, C and D be the gels stemming from the fractions B, C and D respectively.

A rheology measurement (frequency scan—from 0.01 to 100 Hz) is conducted for each of the gels B, C and D.

A comparison of the values of G' (=elastic modulus), G" (=viscous modulus) and of tan δ=G"/G' is carried out at 1 Hz, the results are shown in Table 1.

TABLE 1

| Formulation | G' (1 Hz) (Pa) | G" (1 Hz) (Pa) | Tan δ (1 Hz) |
| --- | --- | --- | --- |
| Gel B | 83 | 37 | 0.446 |
| Gel C (according to the invention) | 69 | 38 | 0.550 |
| Gel D (ref.) | 68 | 37 | 0.544 |

The gels C (according to the invention) and D (reference gel without lidocaine) have equivalent rheological (flow) properties, unlike the gels of the state of the art with lidocaine.

The gel B with lidocaine alone, has different flow properties (G' is higher, tan δ is smaller) relatively to gels C and D. Its behavior in tissues during and after injection is therefore different relative to the reference gel D without lidocaine.

The gels C and D have equivalent sodium hyaluronate concentrations (the gel C has only undergone negligible dilution (of the order of 0.5%) because of the addition of the sodium hydroxide solution).

Example 2

Demonstrating by Rheology the Structural Difference After Sterilization in Humid Heat Between Gels Based on Hyaluronic Acid with and without Lidocaine Hydrochloride and with Lidocaine Hydrochloride and Sodium Hydroxide Let E be a gel based on crosslinked NaHA.

This gel is obtained by hydrating sodium hyaluronate of molecular mass $2.5 \times 10^6$ Da in a 1% by mass sodium hydroxide solution, by adding the crosslinking agent BDDE in order to obtain a crosslinking degree of 11%, by crosslinking for 2 hours at 50° C. and by dialyzing the gel for 24 hours (regenerated cellulose, separation limit: molar mass=60 kDa). The gel thereby obtained has a sodium hyaluronate concentration of 22.7 mg/ml and a pH of 7.12.

After mixing for 10 minutes with a spatula, the gel E thereby obtained is divided into three fractions of equal mass (50 g).

Let F be fraction No.1. In this fraction, 0.3% of lidocaine hydrochloride as a powder is added. The gel is mixed with a spatula for 5 minutes. The pH is then equal to 6.79.

Let g be fraction No.2. In this fraction, 0.3% of lidocaine hydrochloride as a powder is added and then mixing is performed with the spatula for 5 minutes. Next 138 µl of a 2% by mass sodium hydroxide aqueous solution is added and mixed with a spatula for 5 minutes. The pH is 7.25.

Let H be fraction No.3. The gel is mixed with a spatula for 10 minutes. A pH equal to 7.12 is measured.

The gels prepared are introduced into glass syringes and then sterilized with heat (121° C., 20 min). Let F, g and H be the gels stemming from the fractions F, g and H respectively.

A rheology measurement (frequency scan—from 0.01 to 100 Hz) is carried out for each of the gels F, g and H.

A comparison of the values of G'(=elastic modulus), G" (=viscous modulus) and tan δ=G"/G' is carried out at 1 Hz, the results are grouped in Table 2 hereafter.

TABLE 2

| Formulation | G' (1 Hz) (Pa) | G" (1 Hz) (Pa) | Tan δ (1 Hz) |
| --- | --- | --- | --- |
| Gel F | 128 | 62 | 0.484 |
| Gel g (according to the invention) | 90 | 57 | 0.633 |
| Gel H (ref.) | 88 | 55 | 0.625 |

It is noted that the gels g (according to the invention) and H (reference gel without lidocaine) have equivalent flow properties.

The gel F with lidocaine, alone, has different flow properties (G' is higher, tan δ is smaller) relative to gels g and H. Its behavior in the tissues during and after injection is therefore different from that of the reference gel H without lidocaine.

The gels g and H have equivalent sodium hyaluronate concentrations (the gel g has undergone negligible dilution (of the order of 0.3%) because of the addition of the sodium hydroxide solution).

Comparative Example 3

Dilution of the Gel Prepared According to the Prior Art

A gel is prepared according to the manufacturing method described in patent application WO 2010/015901, according to which lidocaine is added as an aqueous solution.

In 50 ml of the gel E of Example 2, having a pH equal to 7.12, 32 µl of an 1% by mass sodium hydroxide aqueous solution are added and then mixed with a spatula for 5 minutes. A pH equal to 7.22 is measured.

A lidocaine hydrochloride aqueous solution is also prepared. For this, 1 g of lidocaine hydrochloride is introduced into 10 ml of water for an injectable preparation and this solution is filtered on a 0.2 µm filter. It is seen that this lidocaine hydrochloride concentration in the solution is close to saturation since if more lidocaine hydrochloride is added into the solution, it proves to be impossible to dissolve this additional supplement of lidocaine hydrochloride.

Next 1.72 ml of the lidocaine hydrochloride solution prepared beforehand is introduced into 50 ml of gel and is then mixed with a spatula for 5 minutes (which involves an increase in the volume of the gel of the order of 3.4%).

The gel obtained is introduced into glass syringes and then sterilized in humid heat (121° C., 20 mins). It is seen that the gel is transparent, without any particles visible to the naked eye.

The preparation method described in patent application WO 2010/015901 therefore does indeed provide the possibility of obtaining a gel based on crosslinked hyaluronic acid and on lidocaine. However, this method involves the addition of a lidocaine hydrochloride solution which generates a significantly larger increase in the volume of the gel than the one induced by the present invention which, itself, does not require addition of lidocaine hydrochloride as a solution but actually as a powder.

Comparative Example 4

Presence of White Particles in the Gel

In 50 ml of the gel E of Example 2, having a pH equal to 7.12, 32 of a 1% by mass sodium hydroxide aqueous solution are added and then mixed with a spatula for 5 minutes. A pH equal to 7.22 is measured.

Next, 0.3% of lidocaine hydrochloride is then added and mixed with the spatula for 5 minutes. It is seen that unlike the preparation method according to the present invention, the fact of adding the lidocaine hydrochloride as a powder after having adjusted the pH to about 7.2, leads to the presence of white particles of lidocaine in the mixture, particles which can then no longer be dissolved into the gel. This also shows the importance of the order for introducing the compounds into the hyaluronic acid gel.

Example 5

Stability of the Gel According to the Invention—Comparison with a Stable Gel of the Prior Art A gel based on crosslinked NaHA is prepared by hydrating sodium hyaluronate with a molecular mass of $3.1 \times 10^6$ Da in a 1% by mass sodium hydroxide solution, by adding the crosslinking agent BDDE in order to obtain a crosslinking degree of 9.2%, by crosslinking for 2 hours at 50° C. and by performing dialysis for 24 hours (regenerated cellulose, separation limit: molar mass=60 kDa). The gel thereby obtained has a sodium hyaluronate concentration of 24.9 mg/ml and a pH of 7.08.

Next 0.3% of lidocaine hydrochloride is added and the gel is mixed with a spatula for 5 minutes. The pH measured is 6.77.

Finally, 144 µl of a 2% by mass sodium hydroxide aqueous solution are added and mixed with a spatula for 5 minutes. The final pH is 7.26.

The gel thereby prepared is introduced into glass syringes and then sterilized with heat (131° C., 2 mins).

Let X be the gel obtained. The gel X has a homogeneous aspect and is transparent, it does not contain any particles visible to the naked eye.

The pH and osmolarity of the gel X are measured. One obtains:
pH=7.23 at the temperature of 23° C.
osmolarity=316 mOsm/kg The lidocaine hydrochloride concentration of the gel X is assayed by HPLC in three different syringes in order to confirm the homogeneity of the active ingredient within the gel. The average value of 0.29±0.01 mg/ml is measured for the three syringes tested.

The rheological properties of the gel X are measured (frequency scan—from 0.01 to 100 Hz) which are grouped in Table 3 hereafter.

TABLE 3

| Formulation | G' (1 Hz) (Pa) | G" (1 Hz) (Pa) | Tan δ (1 Hz) |
|---|---|---|---|
| Gel X | 152 | 56 | 0.37 |

The stability over time of the gel X was then compared with a product with lidocaine of the prior art considered as stable.

The comparative product is Juvéderm® Ultra 3, a commercial product based on crosslinked NaHA (25 mg/ml) and on lidocaine (3 mg/ml i.e. 0.3% by mass), obtained with a manufacturing method (WO 2010/015901) different from the one of the present invention.

The stability of both products over time is evaluated by rheology of t=0, at t=3 months and at t=6 months, by maintaining the products at a storage temperature of 40° C.

The following values of G' (=elastic modulus) at 1 Hz are obtained, grouped in Table 4 hereafter:

TABLE 4

|  | Gel X | Comparative product Juvéderm ® Ultra 3 |
|---|---|---|
| G'(1 Hz) at t = 0 | 152 Pa | 158 Pa |
| G'(1 Hz) at t = 3 months at 40° C. | 107 Pa | 114 Pa |
| G'(1 Hz) at t = 6 months at 40° C. | 93 Pa | 93 Pa |

Both products Gel X and Juvéderm® Ultra 3, have equivalent time-dependent changes of their rheology.

The method according to the invention therefore leads to a hydrogel of hyaluronic acid which has an equivalent degradation from the rheological point of view to those of gels of the prior art, considered as stable over time.

The invention claimed is:

1. A method for obtaining an injectable hydrogel comprising crosslinked hyaluronic acid, or a salt thereof, and lidocaine, the method comprising the following successive steps:
   i) making a gel comprising crosslinking hyaluronic acid or one of its salts with butanediol diglycidyl ether (BDDE),
   ii) adding lidocaine hydrochloride as a powder in the gel and then mixing,
   iii) adjusting the pH to a value of between 6.5 and 7.6 by adding an alkaline agent to the gel and lidocaine hydrochloride mixture, and homogenizing the mixture to obtain a hydrogel which does not contain any suspended solid lidocaine particles, and
   iv) sterilizing the hydrogel with heat,
wherein following the addition of the alkaline agent at step iii), a dilution percentage of the gel is less than or equal to 2.5%, and wherein the dilution percent is defined as V1*100/(V1+V2), wherein V1 is the volume of the added alkaline solution and V2 is the volume of the gel after adding lidocaine hydrochloride and before adding the alkaline solution.

2. The method of claim 1, wherein the concentration of the hyaluronic acid or of one of its salts obtained in step i) is between 1 mg/ml and 50 mg/ml.

3. The method of claim 2, wherein the concentration of the hyaluronic acid or of one of its salts obtained in step i) is between 4 and 40 mg/ml.

4. The method of claim 3, wherein the concentration of the hyaluronic acid or of one of its salts obtained in step i) is between 14 and 35 mg/ml.

5. The method of claim 1, wherein the molecular mass of the hyaluronic acid or of one of its salts is between 1,000 daltons (Da) and $10 \times 10^6$ Da.

6. The method of claim 5, wherein the molecular mass of the hyaluronic acid or of one of its salts is between $2 \times 10^5$ Da and $5 \times 10^6$ Da.

7. The method of claim 6, wherein the molecular mass of the hyaluronic acid or of one of its salts is between $5 \times 10^5$ Da and $4 \times 10^6$ Da.

8. The method of claim 1, wherein the hyaluronic acid or one of its salts is crosslinked and exhibits a crosslinking degree of between 0.1% and 25%.

9. The method of claim 8, wherein the hyaluronic acid or one of its salts is crosslinked and exhibits a crosslinking degree of between 0.5% and 15%.

10. The method of claim 9, wherein the hyaluronic acid or one of its salts is crosslinked and exhibits a crosslinking degree of between 1.5% and 14%.

11. The method of claim 1, wherein the lidocaine hydrochloride concentration of the gel is between 0.1 and 50 mg/ml.

12. The method of claim 11, wherein the lidocaine hydrochloride concentration of the gel is between 1 and 30 mg/ml.

13. The method of claim 12, wherein the lidocaine hydrochloride concentration of the gel is between 2 and 20 mg/ml.

14. The method of claim 1, wherein the alkaline agent is selected from the group consisting of sodium bicarbonate, sodium hydroxide and potassium hydroxide.

15. The method of claim 1, wherein the dilution percentage of the gel is less than or equal to 1.5%.

16. The method of claim 15, wherein the dilution percentage of the gel is less than or equal to 1%.

17. The method of claim 1, wherein the pH of the hydrogel before and after sterilization is between 6.5 and 7.6.

18. The method of claim 17, wherein the pH of the hydrogel before and after sterilization is between 6.9 and 7.5.

19. The method of claim 18, wherein the pH of the hydrogel before and after sterilization is between 7.0 and 7.4.

20. The method of claim 19, wherein the pH of the hydrogel before and after sterilization is between 7.1 and 7.3.

21. The method of claim 1, wherein the sterilization of the hydrogel is carried out in humid heat.

* * * * *